(12) United States Patent
Robertson

(10) Patent No.: US 8,485,966 B2
(45) Date of Patent: Jul. 16, 2013

(54) ENDOSCOPE WITH DISTAL TIP HAVING ENCASED OPTICAL COMPONENTS AND DISPLAY ORIENTATION CAPABILITIES

(75) Inventor: David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 527 days.

(21) Appl. No.: 12/769,292

(22) Filed: Apr. 28, 2010

(65) Prior Publication Data

US 2010/0286475 A1 Nov. 11, 2010

Related U.S. Application Data

(60) Provisional application No. 61/176,624, filed on May 8, 2009.

(51) Int. Cl.
*A61B 1/04* (2006.01)

(52) U.S. Cl.
USPC ............................................. 600/129

(58) Field of Classification Search
USPC ........................................ 600/129, 176, 177
See application file for complete search history.

(56) References Cited

U.S. PATENT DOCUMENTS

| | | | |
|---|---|---|---|
| 4,744,647 A | 5/1988 | Meshel et al. | |
| 5,193,526 A * | 3/1993 | Daikuzono | 606/15 |
| 5,497,269 A | 3/1996 | Gal | |
| 6,259,562 B1 | 7/2001 | Shie et al. | |
| 6,296,608 B1 | 10/2001 | Daniels et al. | |
| 6,398,778 B1 | 6/2002 | Gu et al. | |
| 6,873,444 B1 | 3/2005 | Guletsky et al. | |
| 6,894,358 B2 | 5/2005 | Leib et al. | |
| 6,911,392 B2 | 6/2005 | Bieck et al. | |
| 7,060,933 B2 | 6/2006 | Burrowes et al. | |
| 2001/0003142 A1 | 6/2001 | Koshikawa | |
| 2004/0252188 A1 | 12/2004 | Stantchev et al. | |
| 2005/0003103 A1 | 1/2005 | Krupa | |
| 2005/0049462 A1 * | 3/2005 | Kanazawa | 600/170 |
| 2005/0080318 A1 | 4/2005 | Squicciarini | |
| 2007/0249907 A1 | 10/2007 | Boulais et al. | |
| 2008/0004492 A1 | 1/2008 | Nakamura et al. | |
| 2008/0143822 A1 | 6/2008 | Wang et al. | |
| 2010/0198009 A1 | 8/2010 | Farr et al. | |

OTHER PUBLICATIONS

International Search Report and Written Opinion for International Application No. PCT/US2010/032725, mailed on Jun. 16, 2011, (15 pages).
"Laser Engraved Crystal," Eyetronics, Mar. 3, 2010, 1 page.
"Internal sculpturing of glass by subsurface laser engraving," Fraunhofer Institute for Material and Beam Technology IWS Dresden, 2006, 2 pages.

* cited by examiner

Primary Examiner — WB Perkey
(74) Attorney, Agent, or Firm — Bookoff McAndrews, PLLC

(57) ABSTRACT

An apparatus according to one embodiment includes an endoscope tip including a housing that is monolithically formed of a transparent material. At least one optical component is at least partially encased within the housing. The optical component can be, for example, a light source, a fiber optic, an imaging sensor, a lens, a reflector or a light shield. In another embodiment, an apparatus includes an endoscope having a distal end portion that includes a housing. The housing is monolithically formed with a transparent material and a light source is at least partially encased within the housing. The housing also includes a micro-defects portion within the transparent material of the housing. The micro-defects portion is configured to provide a selected output shape of a beam of light produced by the light source.

15 Claims, 6 Drawing Sheets

ENDOSCOPE WITH DISTAL TIP HAVING ENCASED OPTICAL COMPONENTS AND DISPLAY ORIENTATION CAPABILITIES

CROSS REFERENCE TO RELATED APPLICATION

This patent application claims the benefit of priority under 35 U.S.C. §119 to U.S. Provisional Patent Application No. 61/176,624, filed May 8, 2009, which is herein incorporated by reference in its entirety.

FIELD OF THE INVENTION

The invention relates generally to medical devices and more particularly to endoscope devices and methods for using such devices

BACKGROUND OF THE INVENTION

A variety of different types of endoscopes can be used in various medical, dental, and veterinary applications. Some known endoscopes include optical components such as a light source, an image sensor and/or lenses, at a distal end of the endoscope. It is often desirable to provide light focusing capabilities within the endoscope through the use, for example, of lenses or other optical components coupled to the endoscope distally, near a light source (e.g., fiber optic or LED), or near an image sensor (e.g., CCD). Such components are typically coupled to a structure at the distal end of the endoscope. For example, in some known endoscopes, a lens is glued to a distal end of an optical fiber. In such a case, the lens may not be precisely positioned on the optical fiber because the glue adhering the lens to the endoscope may not have been uniformly applied, or the lens may have moved relative to the position of the optical fiber before the glue has completely dried. In addition, optical components can become loose or detached from the endoscope during use. This can result in reduced quality of images gathered during an endoscopic procedure and/or components can become detached from the endoscope and disposed within the patient's body. Moreover, some known endoscopes are designed for multiple use and require sterilization prior to re-use. The sterilization procedure can be expensive and subject the delicate endoscope components (e.g., lenses) to a harsh environment that may crack or otherwise damage the endoscope components, rendering the endoscope inoperable.

In addition, some known endoscopes use a diffuser to shape an illumination beam from an optical fiber or LED light source to more closely match the field of view of the imager. The diffuser is typically formed with a different material than the endoscope tip, This, together with the small size required of the diffuser, can make such a diffuser difficult to manufacture.

In some known endoscope systems, it can be difficult for the practitioner to discern the orientation of an image as he or she navigates the endoscope tip through a body lumen. If the practitioner misinterprets the orientation of the image, it can be difficult for the practitioner to relocate an area of interest during a subsequent procedure. In some cases, it may be desirable to adjust an image so that certain features (e.g., polyps, cysts) are displayed in a particular orientation, such as for example, in an upright or sideways orientation.

Thus, a need exists for an improved endoscope and endoscope tip that can provide various light focusing capabilities and that is also cost-effective to manufacture. In addition, a system that provides the practitioner with the ability to manipulate the orientation of an image is also needed.

SUMMARY OF THE INVENTION

Embodiments of the present disclosure provide apparatuses and methods related to endoscopes.

An aspect of the present disclosure includes an apparatus which may include an endoscope tip having a housing in which the housing may be monolithically formed of a transparent material. The apparatus may further include at least one optical component at least partially encased within the housing.

Various embodiments of the disclosure may include one or more of the following aspects: the optical component may be a light emitting diode; the optical component may be a fiber optic coupled to an illumination source disposed outside the housing of the endoscope tip; the optical component may be a light source and the apparatus may further include a light shield encased within the housing of the endoscope tip; the optical component may be a light source and the apparatus may further include a light shield encased within the housing of the endoscope tip in which the light shield may have an opacity different than an opacity of the housing of the endoscope tip; the housing may define a working channel which may be configured to receive a medical tool therethrough; a reflector encased within the housing of the endoscope tip in which at least a portion of the reflector may be disposed between a light source and an exterior surface of the endoscope tip; the endoscope tip may include a micro-defects portion defined within the housing of the endoscope tip in which at least a portion of the micro-defects portion may be disposed between a light source and a distal end of the endoscope tip; the endoscope tip may have an external surface defining an optical lens surface; and the transparent material may have a predefined transmissivity for a plurality of wavelengths.

Another aspect of the present disclosure includes an apparatus having an endoscope with a distal end portion including a housing. The housing may be monolithically formed with a transparent material and a light source may be at least partially encased within the housing. The housing may further include a micro-defects portion disposed within the transparent material of the housing.

Various embodiments of the disclosure may include one or more of the following aspects: the micro-defects portion may be configured to provide a selected output shape of a beam of light produced by the light source; an optical component may be at least partially encased within the housing and in the housing may be monolithically formed about the optical component; the housing may define a cavity and the apparatus may further include an optical component at least partially disposed within the cavity of the housing, and the optical component may have an external surface entirely surrounded by a continuous boundary formed by the housing; an image detector may be at least partially encased within the housing; and the housing may define a lumen configured to receive a medical tool therethrough.

A further aspect of the disclosure includes an apparatus having an endoscope including an elongate member and an image detector disposed at a distal end portion of the elongate member. The image detector may be configured to generate an image signal. The apparatus may further include a handle coupled to the elongate member of the endoscope and an actuator coupled to the handle. The actuator may be configured to be actuated by a user to modify an orientation of an image when the image is displayed on an image display device and the image may be associated with the image signal.

Various embodiments of the disclosure may include one or more of the following aspects: a processor operatively coupled to the actuator and configured to send a signal to the image display device to modify the orientation of the image; a processor operatively coupled to the actuator and configured to send a signal to the image display device to display a mark within the image when the image is displayed on the image display device, a location of the mark within the displayed image may be associated with an orientation of the image relative to an endoscope; the actuator may be a first actuator and the apparatus may further include a second actuator coupled to the handle and the second actuator may be configured to be selectively actuated by a user to send a signal to the image display device such that a mark may be displayed within an image, and the mark may indicate a location of an area of interest within the image when the image is displayed; the endoscope may include a housing disposed at the distal end portion of the endoscope, the housing may be formed with a transparent material and the image detector may be at least partially encased within the housing; and the endoscope may include a housing disposed at the distal end portion of the endoscope, the housing may be formed of a transparent material and may include a micro-defects portion formed in at least a portion of the housing.

Another aspect of the present disclosure may include a method of inserting an endoscope into a body lumen of a patient and imaging the body lumen with an image detector of the endoscope. The method may further include actuating an actuator coupled to a handle of the endoscope such that an orientation of an image of the body lumen may be modified when displayed on an image display device.

Various embodiments of the disclosure may include one or more of the following aspects: the actuator may be a first actuator and the method may further include actuating a second actuator to send a signal to the image display device such that a mark may be displayed within the displayed image of the body lumen at an area of interest; and the actuating may include rotating the actuator relative to the handle of the endoscope such that a reference mark on the actuator may be at a desired rotational location relative to the handle and the rotational location of the reference mark may be associated with an orientation of the displayed image relative to the endoscope.

Additional objects and advantages of the invention will be set forth in part in the description that follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

DESCRIPTION OF THE EMBODIMENTS

Figure 1:
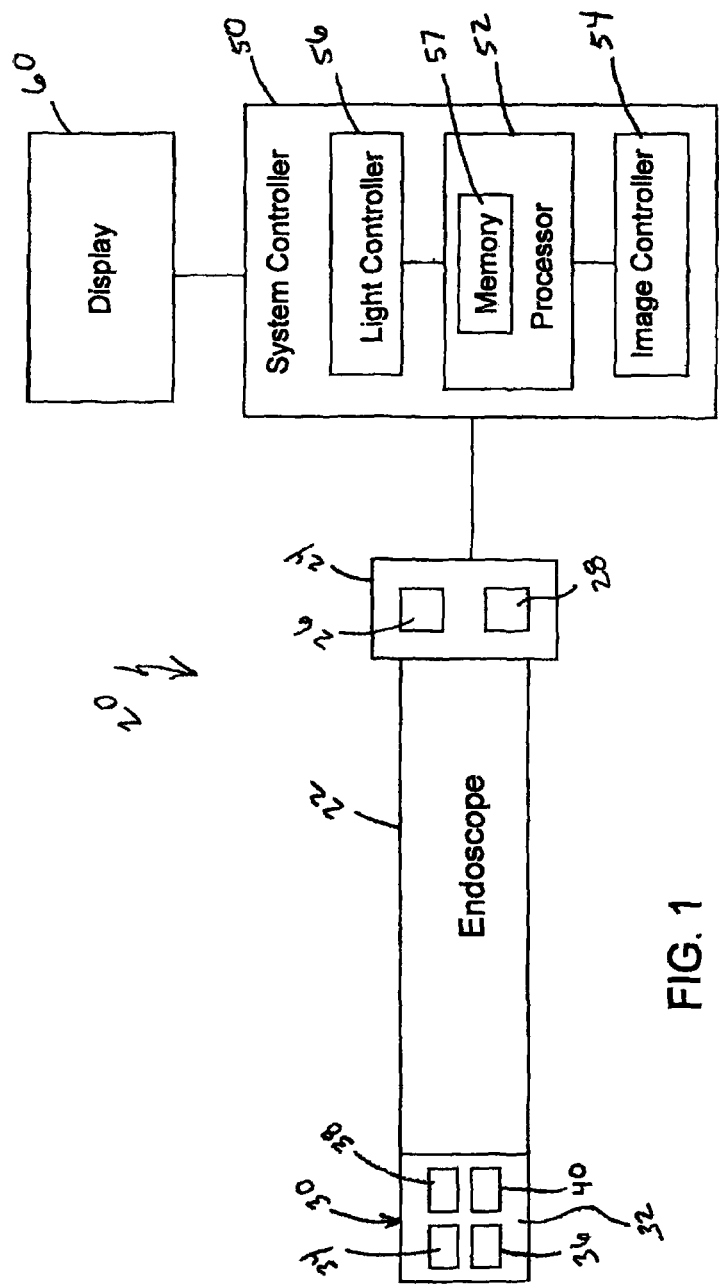
FIG. 1 is a schematic illustration of an endoscope system according to an embodiment.

Reference will now be made in detail to the present embodiments (exemplary embodiments) of the invention, examples of which are illustrated in the accompanying drawings. Wherever possible, the same reference numbers will be used throughout the drawings to refer to the same or like parts.

Endoscopes and methods of using endoscopes are described herein. In one embodiment, an endoscope includes an endoscope tip having a unitary housing that encases various optical components. For example, such optical components can include image detectors, light sources, fiberoptics, light shields, lenses, etc. The housing can be formed with a transparent material that can be processed to induce micro-defects within the housing. Such micro-defects can provide light diffusing capabilities. The micro-defects can be formed with a variety of different patterns to shape an illumination beam of light from a light source (e.g., a fiberoptic or LED light source). In some embodiments, an endoscope system includes an endoscope that permits the user to alter the orientation of the display of an image captured using the endoscope.

An apparatus according to one embodiment includes an endoscope tip including a housing that is monolithically formed of a transparent material. At least one optical component is at least partially encased within the housing. The optical component can be, for example, a light source, a fiber optic, an imaging sensor, a lens, a reflector, a diffuser, a filter, or a light shield. In another embodiment, an apparatus includes an endoscope having a distal end portion that includes a housing monolithically formed with a transparent material. A light source is at least partially encased within the housing. The housing also includes a micro-defects portion within the transparent material of the housing. The micro-defects portion can be configured to provide a selected output shape of a beam of light produced by the light source. The micro-defects portion can also form lenses, provide focusing or filtering capabilities, as well as diffusion. In some embodiments, micro-defects can also be formed within a fiberoptic light source.

In another embodiment, an apparatus includes an endoscope that includes an elongate member and an image detector disposed at a distal end portion of the elongate member. The image detector is configured to generate an image signal. A handle is coupled to the elongate member of the endoscope and an actuator is coupled to the handle. The actuator is configured to be actuated by a user to modify an orientation of an image when the image is displayed on an image display device. The image is associated with the image signal.

In one embodiment, a method includes inserting an endoscope into a body lumen of a patient. The body lumen is then imaged with an image detector of the endoscope. An actuator that is coupled to a handle of the endoscope is actuated such that an orientation of an image of the body lumen is modified when displayed on an image display device. In some embodiments, the method further includes actuating a second actuator to send a signal to the image display device to cause a mark to be displayed within the displayed image of the body lumen at an area of interest.

It is noted that, as used in this written description and the appended claims, the singular forms "a," "an" and "the" include plural referents unless the context clearly dictates otherwise. Thus, for example, the term "a fiberoptic" is intended to mean a single fiberoptic or a combination of fiberoptics. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the endoscope end inserted inside a patient's body would be the distal end of the endoscope, while the endoscope end outside a patient's body would be the proximal end of the endoscope.

FIG. 1 is a schematic representation of an endoscope system according to an embodiment of the invention. An endoscope 20 includes an elongate member 22 that can be inserted at least partially into a body lumen (not shown in FIG. 1), a distal endoscope tip 30, and a handle 24 that is configured to be disposed outside the body lumen. The elongate member 22 can be flexible, or can include a portion that is flexible, to allow the elongate member to be maneuvered within the body lumen. The endoscope 20 can be inserted into a variety of different body lumens such as, for example, a ureter, a gastrointestinal lumen, an esophagus, a vascular lumen, etc. The handle 24 can include one or more control mechanisms or actuators 26 that can be used to control and maneuver the elongate member 22 of the endoscope 20 through the body lumen. The endoscope 20 can also include an actuator 28 that can be used to actuate other functions of the endoscope 20, such as to control or maneuver lenses, image detectors and/or other components associated with illuminating and/or capturing images within a body lumen.

The endoscope tip 30 can be coupled to a distal end portion of the elongate member 22. The endoscope tip 30 includes a housing 32 that can be formed, for example, with a plastic or glass material. In some embodiments, the housing 32 is formed with a transparent material and can be configured, for example, to filter or enhance certain wavelengths of light. The material used to form the housing 32 can be selected based on a material's particular optical properties, such as its ability to transmit light of a particular wavelength(s). The housing 32 can be, for example, molded or post processed to form optically transmissive regions. The housing 32 can be monolithically formed (e.g., formed in one piece) or constructed of multiple components, for example, adhesively bonded together.

The housing 32 can encase various imaging or optical components. For example, optical components, such as one or more lenses 34, an image detector 36, and/or a light source 38 can be at least partially encased or embedded within the housing 32. For example, optical components can be at least partially disposed within a cavity in the housing 32. In some embodiments, optical components can be insert molded within the material of the housing 32 such that they are entirely surrounded or encased by the housing 32. The encasing and/or partial encasing of such optical components within the housing 32 can prevent or limit contact between the optical component and an interior of the patient's body. The housing 32 can protect the optical components from damage and reduce the risk that the optical components will become dislodged during use of the endoscope 20 within a patient's body.

The housing 32 can define openings in communication with a cavity within the housing 32. Some optical components can extend partially within a cavity of the housing 32. For example, an optical component can extend within a cavity of the housing 32 such that a distal end portion of the optical component is encased within the housing 32 and a proximal end portion of the component can extend out a proximal end of the housing 32 and through a lumen (not shown in FIG. 1) of the elongate body 122. For example, optical components having a power line or signal line, such as light source 38 or image detector 36, can have the power line or signal line extending out of the proximal end of the housing 32.

Other types of optical components (not shown in FIG. 1) can also be encased within the housing 32, such as for example, directional baffling, shielding or reflectors. Such components can be used to direct illumination toward or away from a desired region. For example, a light shield can be used to reduce or minimize the transmission of light to certain areas within the endoscope tip 30 or within the inspection site within a body lumen of the patient. A light shield can be formed, for example, by introduction of material of increased opacity from the material of the housing 32. A reflector, can be formed, for example, with a reflective metallic material, and can be used, for example, to reflect and/or focus light from the light source 38 to the inspection site within the body lumen.

Although three optical components (lens 34, image detector 36, light source 38) are illustrated in FIG. 1, any combination and sub-combinations of components can be included within the endoscope tip 30. The housing 32 can also define various optical surfaces (not shown in FIG. 1) used to modify light provided by a light source. Such an optical surface can be, for example, a depression or other modification of an outer surface of the housing 32 of the endoscope tip 30 to define light focusing and/or dispersing effects.

In some embodiments, the housing 32 includes a micro-defect portion 40 for diffusing, focusing, converging, or filtering light from a light source (e.g., light source 38). For example, the micro-defect portion 40 can be used to shape an illumination beam from an optical fiber to match more closely the field of view of an imager. Typically, such diffusion is accomplished by placing a separate diffuser component over an output end of an optical fiber. In such a case, because the diffuser is a different medium than the distal end of the endoscope, and due to the small size requirements for this type of diffuser, such diffusers can be difficult to manufacture. Here, however, the micro-defect portion 40 can be formed, for example, by mechanical roughing of a surface of the housing 32, or introduction of small particles of another substance or gas bubbles into the housing 32 that deflect and/or diffuse the light provided by the light source.

In some embodiments, a micro-defect portion 40 is formed within the housing 32 by laser processing. For example, in a housing 32 formed with a transparent material, micro-defects can be laser-induced into the housing 32, for example, at a location that is at least partially within the path of light output from a light source (e.g., an optical fiber or a LED). In some embodiments, micro-defects can be induced or formed through other energy sources, such as, for example, a High Intensity Focused Ultrasound (HIFU), or with particle beams. Such defects can be a variety of different shapes, sizes and/or patterns, such as, for example, concentric circles, stripes, or spots. Multiple micro-defect portions 40 can also be provided (e.g., individual defects or groups of defects). Individual micro-defects can have variable spacing resulting in variable densities within the housing 32. The defects can be placed radially from an optical axis and/or at various depths within the housing 32. Such micro-defect inducing techniques, such as laser-inducing techniques, can also be used on an end portion of an optical fiber itself to shape an output beam of the optical fiber. In such an embodiment of an endoscope, an endoscope tip 30 may not be included.

In some embodiments, micro-defects can be formed such that they impart an apparent color to the medium in which they are induced (e.g., the housing 32). Such defects can be produced to block or pass selected wavelengths to act as a filter, for example, of red, blue, green or infrared wavelengths. Micro-defects can also be used to produce reflective surfaces within the housing 32. The reflective surfaces can be of specific wavelengths or a band of wavelengths. Micro-defects can also be used to produce lensing effects over or around a light source or imaging sensors.

The light source 38 can be, for example, a light emitting diode (LED) or an optical fiber. Light can be provided by more than one optical fiber, or a bundle of optical fibers. The proximal end of the optical components may be coupled to an external light source capable of providing light of a desired wavelength or wavelengths. An LED light source can also provide light of various wavelengths. The image sensor 36 can be, for example, a solid-state image sensor, such as a charged coupled device (CCD), a charge injection device (CID), a photodiode array (PDA) or complementary metal oxide semiconductors (CMOS). The lens 34 can be formed with for example, glass or plastic. The lens 34 can be either separate from or attached directly to the image sensor 36.

The endoscope 20 can also include one or more lumens (not shown in FIG. 1) extending through the elongate member 22 and/or handle 24. In some embodiments, the elongate member 22 of the endoscope 20 can include a single lumen that can receive therethrough various components. For example, optical fibers or electrical wires can pass through a lumen of the endoscope 20 to provide illumination, imaging capabilities, power, and/or signals at or from a distal end portion of the endoscope 20. For example, the endoscope 20 can include imaging optical fibers and/or illumination optical fibers (not shown in FIG. 1). The endoscope 20 can also be configured to receive various medical devices or tools (not shown in FIG. 1) through one or more lumens of the endoscope 20, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel is defined by the endoscope 20 and coupled at a proximal end to a fluid source (not shown in FIG. 1). The fluid channel can be used to irrigate an interior of a body lumen. In some embodiments, an eyepiece can be coupled to a proximal end portion of the endoscope 20, for example, adjacent the handle 24, and coupled to an optical fiber that can be disposed within a lumen of the endoscope 20. Such an embodiment allows a physician to view the interior of a body lumen through the eyepiece.

A system controller 50 can be coupled to the endoscope 20 and configured to control various elements of the endoscope 20 as described in more detail below. The system controller 50 can include, for example, a processor 52, an image controller 54, and a light controller 56. The light controller 56 can include an external light source for providing light to the light source 38 of the endoscope 20. In some embodiments, a filter device and/or a spectrometer (not shown in FIG. 1) are also provided. The external light source can be configured to provide light at various different wavelengths. For example, the external light source can send light at various wavelengths associated with visible light, infrared light and/or ultraviolet light. The image controller 54, the processor 52 and/or the light controller 56 can be coupled to an image or video display device 60 (e.g., a computer, a monitor or other known image display device) via the system controller 50 or by a separate connection. Thus, in alternative embodiments, some or all of these devices can be provided as separate components, separate from the system controller 50.

The image detector 36 can be coupled to the imaging controller 54 via electrical wires that pass through a lumen of the endoscope 20 as described above. Thus, images of a body lumen can be captured by the image detector 36 and processed by the image controller 54. The images can also be displayed on the image display device 60.

As stated above, the light source 38 can include illumination fibers (not shown in FIG. 1) that can be coupled to the light controller 56. The illumination fibers can be used to transfer light from an external light source (not shown in FIG. 1), through the endoscope 20, and into a body lumen. The illumination fibers can be formed, for example, with a quartz material or other suitable glass or polymer material capable of sending and receiving various wavelengths of light. The illumination fibers can be a single fiber or a bundle of multiple fibers.

In some embodiments, the endoscope 20 can also include imaging fibers (not shown in FIG. 1) (rather than or in addition to an image detector 36) that can be disposed through a lumen of the endoscope 20 and can be coupled to the system controller 50. The imaging fibers can be disposed through the same or different lumen of the endoscope 20 as the illumination fibers. Images of a body lumen and/or an object within the body lumen can be captured and processed by the image controller 54 or a spectrometer (not shown). The captured and processed images can also be displayed on the image display device 60. Imaging fibers can also be used to send light to a spectrometer (not shown in FIG. 1) for a spectral analysis of the interior of the body lumen.

The processor 52 of the systems controller 50 can be operatively coupled to the light controller 56 and the image controller 54. The processor 52 (e.g., central processing unit (CPU)) includes a memory 57 that can store and process images or other data received from the endoscope 20. The processor 52 can analyze images, and calculate and analyze various parameters and/or characteristics associated with an image or other data provided by the endoscope 20. The processor 52 can also be operatively coupled to the various components of the system controller 50. As stated above, in alternative embodiments, the light controller 35, the image controller 54 and/or processor 52 are separate devices and can be coupled to the endoscope 20 using a separate connector or connectors. In such an embodiment, the image controller 54 and light controller 56 can optionally be coupled to each other and/or the system controller 50.

The processor 52 can be, for example, a commercially-available personal computer, or a less complex computing or processing device that is dedicated to performing one or more specific tasks. For example, the processor 52 can be a terminal dedicated to providing an interactive graphical user interface (GUI). The processor 52, according to one or more embodiments of the invention, can be a commercially-available microprocessor. Alternatively, the processor 52 can be an application-specific integrated circuit (ASIC) or a combination of ASICs, which are designed to achieve one or more specific functions, or enable one or more specific devices or applications. In yet another embodiment, the processor 52 can be an analog or digital circuit, or a combination of multiple circuits.

The memory 57 of the processor 52 can store code representing instructions to cause the processor 52 to perform a process. Such code can be, for example, source code or object code. The code can cause the processor 52 to perform various techniques for processing images taken with an endoscope. The processor 52 can be in communication with other processors, for example, within a network, such as an intranet, such as a local or wide area network, or an extranet, such as the World Wide Web or the Internet. The network can be physically implemented on a wireless or wired network, on leased or dedicated lines, including, for example, a virtual private network (VPN).

The memory 57 of the processor 52 can include one or more types of memory. For example, the memory 57 can include a read only memory (ROM) component and a random access memory (RAM) component. The memory 57 can also include other types of memory that are suitable for storing data in a form retrievable by the processor. For example, electronically programmable read only memory (EPROM), erasable electronically programmable read only memory (EEPROM), flash memory, as well as other suitable forms of memory can be included within the memory 57. The processor 52 can also include a variety of other components, such as for example, co-processors, graphic processors, etc., depending, for example, upon the desired functionality of the code.

The processor 52 can store data in the memory 57 or retrieve data previously stored in the memory 57. The components of the processor 52 can communicate with devices external to the processor 52, for example, by way of an input/output (I/O) component (not shown). According to one or more embodiments, the I/O component can include a variety of suitable communication interfaces. For example, the I/O component can include, for example, wired connections, such as standard serial ports, parallel ports, universal serial bus (USB) ports, Svideo ports, local area network (LAN) ports, small computer system interface (SCCI) ports, and so forth. Additionally, the I/O component can include, for example, wireless connections, such as infrared ports, optical ports, Bluetooth® wireless ports, wireless LAN ports, or the like.

The endoscope 20 can be coupled to the system controller 50 and/or the various components described in association of the system controller 50 (e.g., light controller 56, processor 52, image controller 54) with cables or wires or can include a wireless connection. For example, the endoscope 20 can be configured to provide short range transmission of signals (e.g., image detector or sensor data) from the endoscope 20 (e.g., a processor or chip within the handle) to, for example, the system controller 50 at a location outside of the sterile field. Battery operated electronics and illumination (e.g., battery operated light sources 38) can minimize the number of hard connections needed to operate the endoscope. An endoscope 20 can be configured to transmit data from any point in the process chain from raw pixel value to full video signal.

The endoscope 20 can be used to illuminate and image a body lumen B, and can also optionally be used to identify an area of interest within a body lumen. The endoscope 20 can be inserted at least partially into a body lumen B, such as a ureter, and the light controller 56 and light source 38 can be used to illuminate the body lumen or a portion of the body lumen. The body lumen can be observed while being illuminated via an eyepiece as described above, or the body lumen can be imaged using the image detector 36 and image controller 54. The images can be displayed on the image display device 60.

In embodiments where the endoscope 20 is coupled to a spectrometer, the light intensity and spectrum can also be measured and/or displayed. For example, the portion of the image associated with the area of interest can be measured by the spectrometer.

Figure 2:
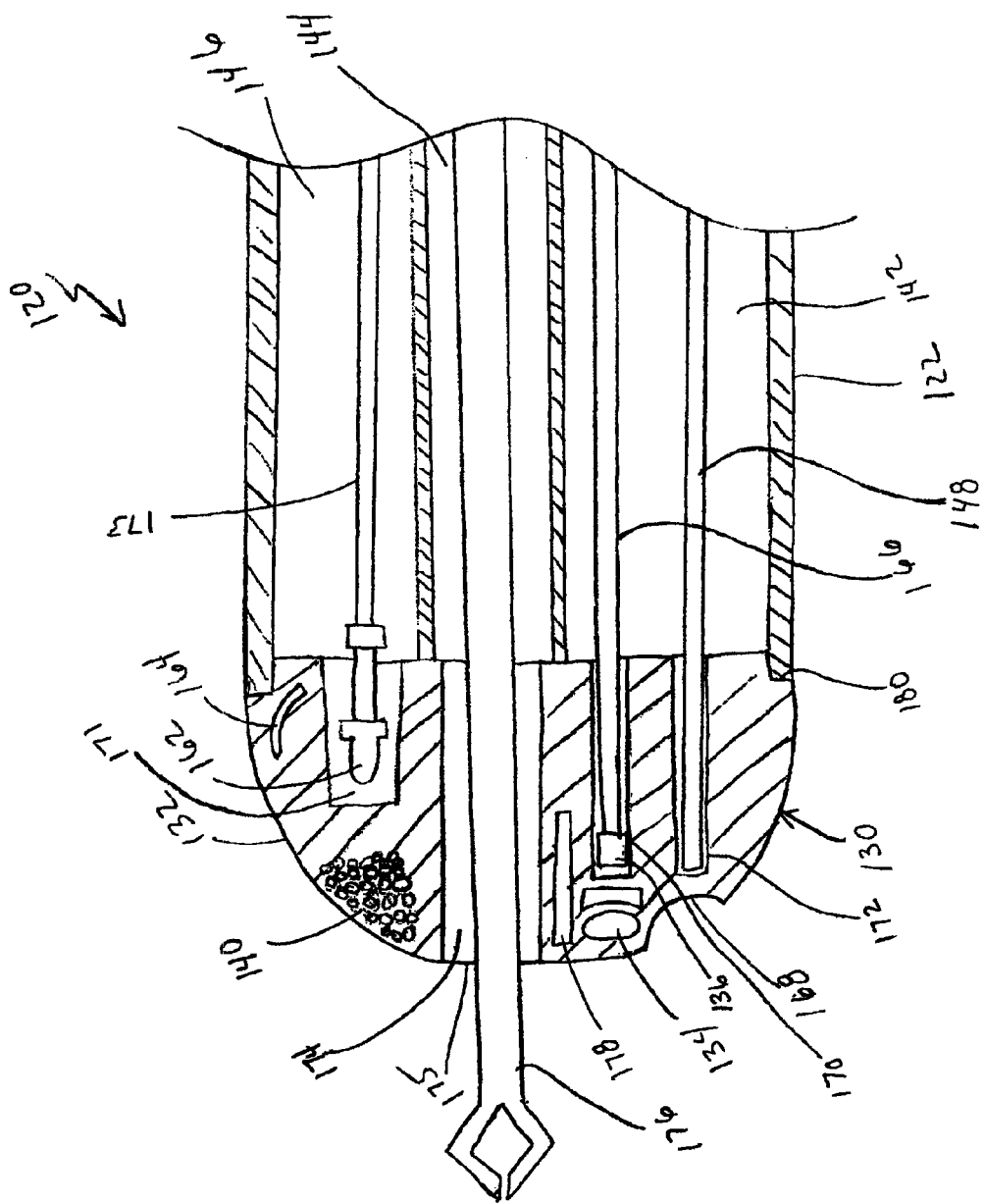
FIG. 2 is a side cross-sectional view of a portion of an endoscope according to an embodiment.

FIG. 2 is a cross-sectional view of a distal end portion of an embodiment of an endoscope. An endoscope 120 includes an elongate member 122 and a distal endoscope tip 130 (also referred to as "endoscope tip") coupled to a distal end portion of the elongate member 122. The elongate member 122 defines a first lumen 142, a second lumen 144 and a third lumen 146. The endoscope 120 can be coupled to various control devices (not shown in FIG. 2), such as, for example, a system controller, light controller, image controller and/or an image display device as described with reference to FIG. 1.

The endoscope tip 130 includes a housing 132 formed with a transparent material that encases several optical components. In this embodiment the housing 132 encases (at least partially) multiple different optical components for illustrative purposes to demonstrate the versatility of the endoscope tip 130. In other embodiments, various other combinations of optical components can be encased by the housing 132.

The housing 132 includes an annular flange 180 configured to be coupled to the elongate body 120 with for example, an adhesive, a friction fit connection or other suitable coupling. The housing 132 also defines a lumen 174 that is in communication with the lumen 144 of the elongate body 122. An optical surface 168 is configured to focus or disperse light sent by an illumination optical fiber 148. The housing 132 also defines multiple cavities 170, 171 and 172 in which various optical components can be at least partially disposed. Disposed within cavity 171 is a LED light source 162. The illumination optical fibers 148 is partially disposed within the cavity 172. An image detector 136 (e.g., CCD, CID, PDA, or CMOS) is disposed within cavity 170 and has power and/or signal lines extending from the cavity 170 (e.g., cable 166). The illumination optical fiber 148 is shown in FIG. 2 as a single strand, but it should be understood that such an optical fiber can include one or more optical fibers. For example, illumination optical fibers 148 can include optical fiber bundles. Any of the optical components can also be arrayed proximal to the housing 132, and can be separated, or in contact, or bonded to the housing 132.

In addition to optical components extending within cavities of, or proximal to, the housing 132, several optical components are encased or molded or formed within the material of the housing 132. A lens or multiple lenses 134 are encased within the housing 132 distal to the image detector 136. A light shield 178 is disposed within the housing 132 to at least partially block light emitted from the LED light source from being received by the image detector 136, and a reflector 164 is encased within the housing 132 to help focus or redirect light from the LED light source 162. The housing 132 also includes an example pattern of a diffuser portion 140, which as described above, can include micro-defects within the material of the housing 132. As described above, the micro-defects portion 140 can be configured to diffuse, focus, filter or converge light from the LED light source 162. In some embodiments, such diffusion can permit the endoscope tip 130 to "glow" and softly illuminate the inspection site.

The illumination optical fiber 148 extends through the lumen 142 of the elongate body 122 and can be coupled to, for example, an external light source (not shown) and/or a light controller (not shown). The image detector 136 is coupled to a cable 166 that extends through the lumen 142 and can be coupled to, for example, an image controller (not shown), a power source, and/or a system controller. The LED light source 162 is coupled to a power cable 173 that extends through the lumen 146 of the elongate body 122 and can be coupled to, for example, a power source (not shown) and/or system controller (not shown). A medical tool 176 is shown disposed through the lumen 174 and can extend out an opening 175 and distally of the endoscope tip 130. The medical tool 176 is merely an example of a tool that can be used in conjunction with the endoscope 120.

Figure 3:
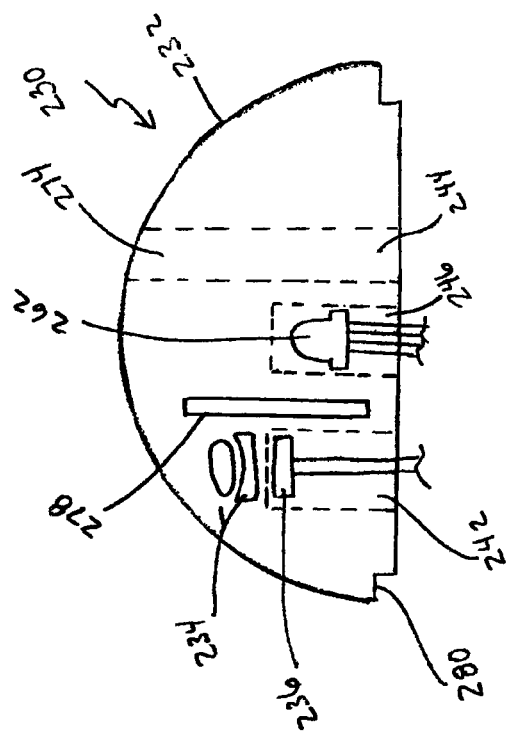
FIG. 3 is a side view of an endoscope tip according to an embodiment.

FIG. 3 illustrates an endoscope tip 230 according to another example embodiment. The endoscope tip 230 can be coupled to an elongate member (not shown) of an endoscope as described above, using a mounting surface 280. The endoscope tip 230 includes a housing 232 formed with a transparent material. In this embodiment, the housing 232 defines a cavity 242, a cavity 246 and a lumen 244, which can each be in communication with a corresponding lumen of an elongate member as described above for endoscope 120. The lumen 244 can be used as a working channel to receive various medical tools. In this embodiment, a LED light source 262 is disposed within cavity 246, and an image detector 236 is disposed within cavity 242. Encased within the housing 232 is a light shield 278 disposed between the LED light source 262 and the image detector 236, and lenses 234 that are disposed distal to the image detector 236. The light shield 278 may also form a complete sleeve around the image detector 236 and lenses 234.

Figure 4:
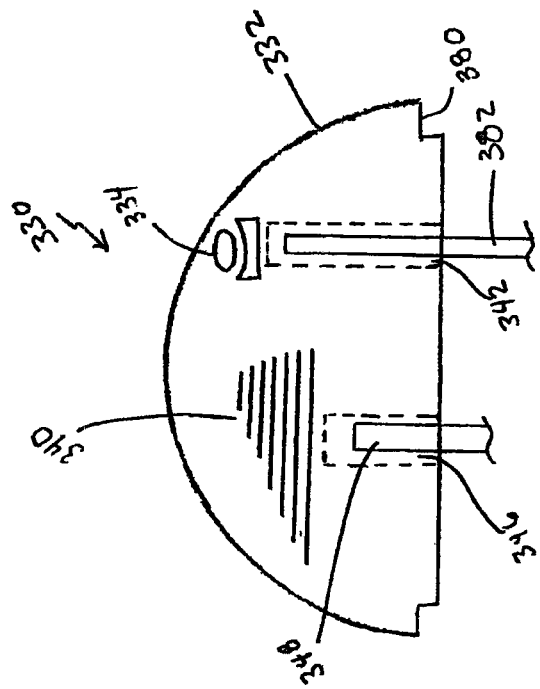
FIG. 4 is a side view of an endoscope tip according to another embodiment.

FIG. 4 is another example of an endoscope tip. An endoscope tip 330 includes a housing 332 formed of a transparent material and that defines a cavity 346 and a cavity 342. The housing 332 can be coupled to an elongate member of an endoscope via mounting surface 380 as described above. In this embodiment, an imaging optical fiber (or optical fibers) 382 is disposed within the cavity 342 and an illumination optical fiber (or optical fibers) 348 is disposed within cavity 346. For example, the imaging fiber 382 can be coupled to an image detector at a proximal end portion of the endoscope 320. As with the previous embodiment, the cavity 346 and the cavity 342 can each be in communication with a corresponding lumen of an elongate member of an endoscope. Lenses 334 are disposed distal to the imaging fiber(s) 382 and a diffuser or micro-defects portion 340 has been induced into the housing 332. As shown in FIG. 4, the diffuser portion 340 illustrates an example of a linear pattern of defects induced within the material of the housing 332. In some embodiments, the lenses 334 can alternatively be disposed within a cavity (not shown) defined by the housing 332 and extending inward from a distal surface of the housing 332. In some embodiments, a distal end of the imaging fibers 382 can terminate at a location proximal to the housing 332 (rather than extending into a cavity in the housing).

Figure 5:
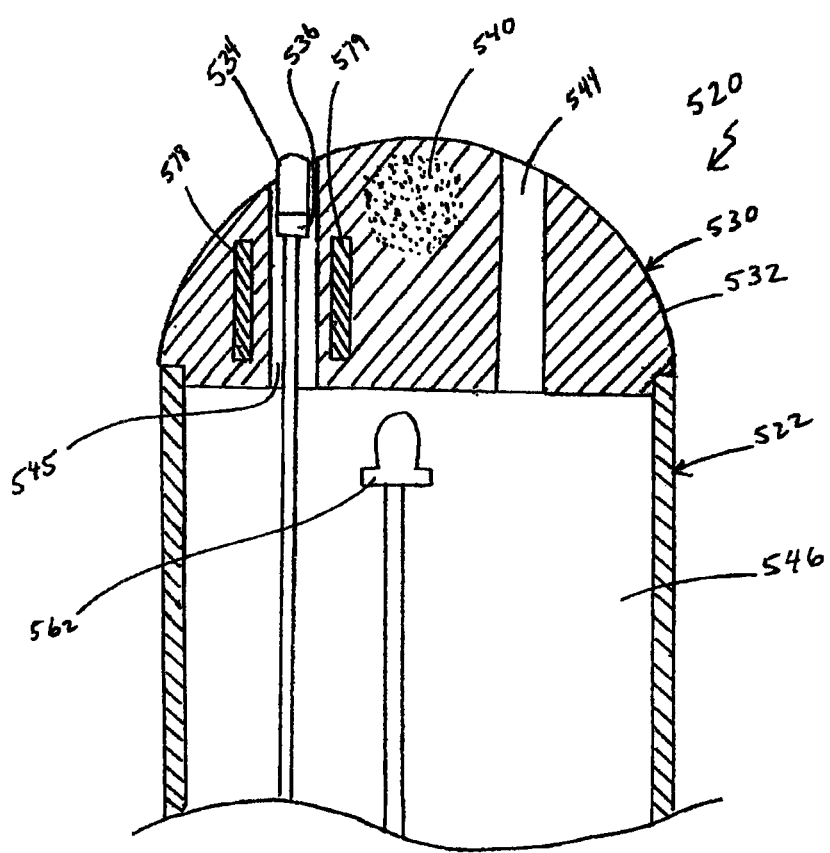
FIG. 5 is a side cross-sectional view of a portion of an endoscope according to another embodiment.

FIG. 5 illustrates an endoscope 520 that includes an endoscope tip 530 according to another example embodiment coupled to an elongate member 522. The endoscope tip 530 can be coupled to the elongate member 522, as described above, using a mounting surface 580. The endoscope tip 530 includes a housing 532 formed with a transparent material. In this embodiment, the housing 532 defines a first lumen 544 and a second lumen 545, which can each be in communication with a lumen 546 (or separate corresponding lumens as described above for endoscope 120) of the elongate member 522. In this embodiment, a LED light source 562 (or alternatively, a fiberoptic light source) is disposed proximal to the endoscope tip 530 within a lumen 546 of the elongate member 522. The first lumen 544 of the endoscope tip 530 can be used as a working channel to receive various medical tools (not shown in FIG. 5). An image detector 536 coupled to a lens stack 534 is disposed within the second lumen 545. Encased within the housing 532 are two light shields 578 and 579 disposed around the image detector 536 and the lens stack 534. It should be understood that more or less than two light shields can alternatively be included. A micro-defects portion 540 is disposed within a portion of the housing 532 to shape the output of the light source.

Figure 6:
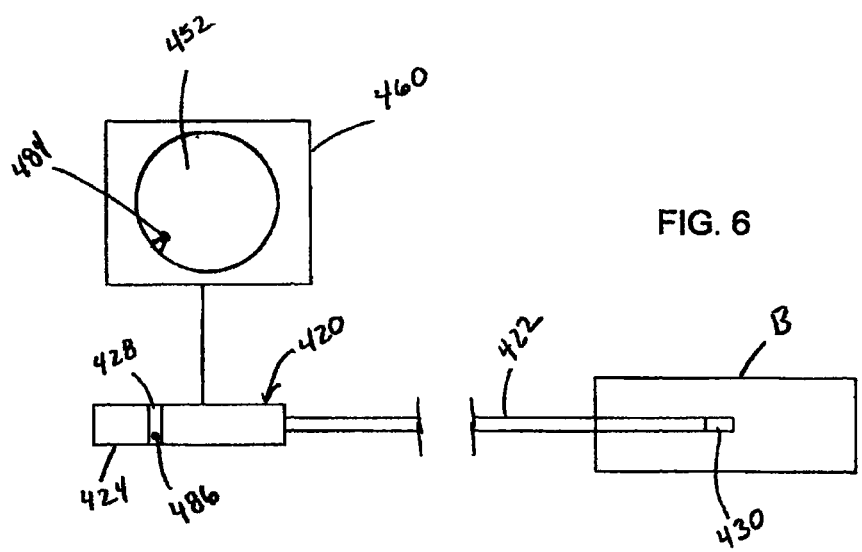
FIG. 6 is a schematic illustration of a portion of an endoscope system according to an embodiment and a schematic representation of a body lumen showing an image on an image display device in a first orientation.
Figure 7:
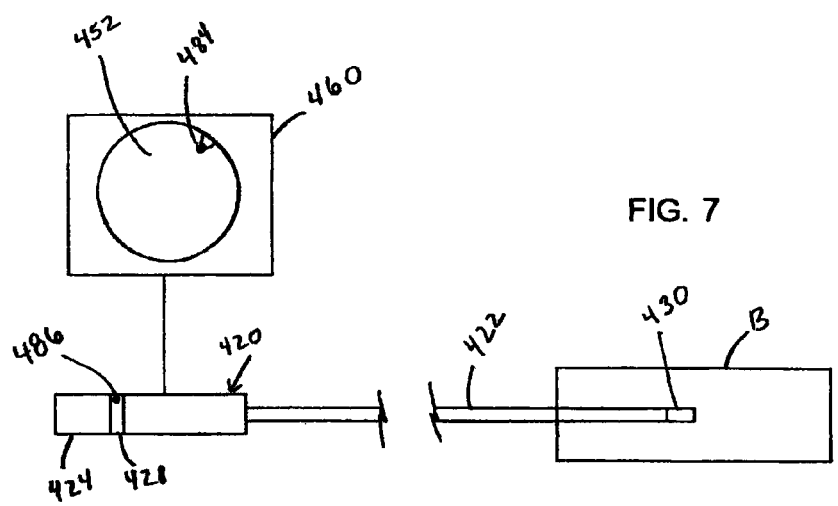
FIG. 7 is a schematic illustration of the portion of the endoscope system and schematic representation of the body lumen of FIG. 6 showing the image on the image display device in a second orientation.

FIGS. 6 and 7 illustrate a portion of an endoscope system according to an embodiment. In this embodiment, an endoscope 420 includes an elongate member 422 and an endoscope tip 430 that can each be configured as described above for previous embodiments. The endoscope 420 can be coupled to a system controller and/or other processing components (not shown in FIGS. 6 and 7). For illustration purposes, FIGS. 6 and 7 show only an image display device 460 coupled to the endoscope 420, but it should be understood that other components discussed above can also be included.

In this embodiment, the endoscope 420 includes an actuator 428 that is coupled to a handle 424 of the endoscope 420 and can be rotated relative to the handle 424. In alternative embodiments, other types of actuators can be used such as, for example, levers, buttons, or knobs.

An image processor (not shown in FIGS. 6 and 7) can be included within the handle 424 and operatively coupled to the image display device 460. The image processor can send a signal to the image display device 460 to cause the display of a mark 484 on an image being viewed on the image display device 460. The mark 484 corresponds to a reference mark 486 on the actuator 428 and represents an orientation of the endoscope 420 and image detector (not shown in FIGS. 6 and 7). For example, as shown in FIG. 6, the endoscope 420 can be inserted into a body lumen B, with the actuator 428 at a first rotational location relative to the handle 424 and an image 452 of the body lumen B can be produced by an image detector (not shown in FIGS. 6 and 7) of the endoscope 420. The image processor (not shown in FIGS. 6 and 7) can send a signal to the image display device 460 to display the image 452 of the body lumen B with the mark 484 visible on the image 452. The location of the mark 484 on the image 452 correlates to the rotational location of the reference mark 486 relative to the handle 424 and an orientation of the endoscope 420.

The orientation of image 452 on the video display 460 can be modified by the practitioner through manipulation of the actuator 428. For example, the actuator 428 can be rotated relative to the handle 424 such that the reference mark 486 on the actuator 428 is located at a different rotational location relative to the handle 424, as shown in FIG. 7. The image 452 will be rotated in the display on the image display device 460 by the number of degrees corresponding to the number of degrees the actuator 428 was rotated relative to the handle 424. The location of the mark 484 viewable on the image 452 will also be moved to maintain a reference to the location of the initial orientation of the endoscope 420 and handle 424 (such as the "top", or "up"). Thus, the practitioner can manipulate an image, such as turning the image to a desired position, through actuation of the actuator 428. In some embodiments, the reference mark 486 can provide a reference to a nominal "top" of an image. In some embodiments, the image processor can be configured to mark the orientation of an image relative to a longitudinal axis of the body lumen.

In some embodiments, an endoscope system can provide electronic image movement tracking capabilities to provide relevant anatomic orientation markers or labeling such as anterior, posterior, cephalad, or the location of pathology or foreign objects, etc. For example, an object or area of interest can be electronically marked or tagged by the user by actuating a selection button (or other type of actuator) with a cursor over the area of interest within an image. Software and/or hardware based image processing tracks the change in location of tagged objects and other landmarks in consecutive video frames. The area of interest can be tracked when the image is moved away by providing, for example, directional arrows pointing to the selected or tagged area of interest to allow the practitioner to quickly return to that area of interest. In such an embodiment, the endoscope can also include a sensor to track the movement of the endoscope after an object has been marked. For example, longitudinal and/or rotational movement of the endoscope can be monitored. The endoscope can also include a calibration processor configured to calibrate a position of the endoscope, and to determine a direction of the arrows pointing to the area of interest within the image relative to the position of the endoscope.

Figure 8:
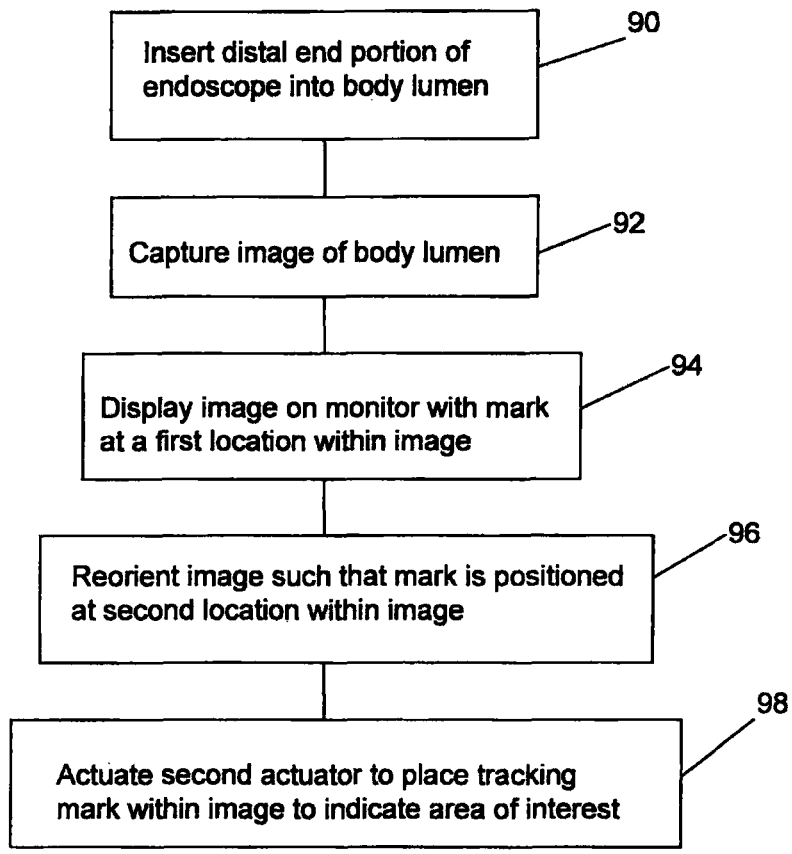
FIG. 8 is a flowchart of a method according to an embodiment.

FIG. 8 is a flowchart of a method of imaging a body lumen. At 90, a distal end portion of an endoscope can be inserted into a body lumen of a patient. At 92, an image is captured of the body lumen (or a portion of the body lumen) using an image detector included at the distal end portion of the endoscope. The image is displayed on an image display device at 94. A mark is displayed at a first location within the image indicating a first orientation of the image relative to the endoscope. At 96, the image is reoriented such that the mark within the image is positioned at a second location within the image. The second location of the mark within the image indicates a second orientation of the image relative to the endoscope. For example, in some embodiments, an actuator on a handle of the endoscope can be rotated such that a reference mark on the actuator is moved from a first position relative to the handle to a second position relative to the handle. The position of the reference mark on the handle can represent a position of the image relative to the endoscope. In some embodiments, at 98, the user can actuate a second actuator to cause a tracking mark to be displayed within an image to mark or tag a selected area of interest within the body lumen. For example, the second actuator can be coupled to the image display device that allows the user to place a cursor over the area of interest within the image and then to place a tracking mark on the image to indicate the location of the area of interest.

Some embodiments relate to a computer storage product with a computer-readable medium (also can be referred to as a processor-readable medium) having instructions or computer code thereon for performing various computer-implemented operations. The media and computer code (also can be referred to as code) may be those specially designed and constructed for the specific purpose or purposes. Examples of computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signals; and hardware devices that are specially configured to store and execute program code, such as Application-Specific Integrated Circuits (ASICs), Programmable Logic Devices (PLDs), and ROM and RAM devices. Examples of computer code include, but are not limited to, micro-code or micro-instructions, machine instructions, such as produced by a compiler, and files containing higher-level instructions that are executed by a computer using an interpreter. For example, an embodiment of the invention can be implemented using Java, C++, or other object-oriented programming language and development tools. Additional examples of computer code include, but are not limited to, control signals, encrypted code, and compressed code.

Although some embodiments herein are described in connection with optical images and the processes performed in connection with these optical images, it should be understood that all such embodiments can be considered in connection with signals (e.g., analog or digital signals) that are associated with or represent these optical images and the related processes. Similarly, to the extent that some embodiments here are described in connection with such signals, it should be understood that all such embodiments can be considered in connection with the associated optical images and the processes with respect to these optical images.

While various embodiments have been described above, it should be understood that they have been presented by way of example only, and not limitation. While embodiments have been particularly shown and described, it will be understood by those skilled in art that various changes in form and details may be made.

For example, the endoscope systems, endoscopes, and/or endoscope tips described herein can include various combinations and/or sub-combinations of the components and/or features of the various embodiments described. The endoscopes described herein can be configured to image various areas within a body. For example, an endoscope can be configured for use to image or illuminate any location within a patient, such as any body lumen or cavity, tissue or organ. The various optical components can be incorporated within a fiberscope or an electronic imaging or illuminating endoscope.

An endoscope according to various embodiments can have a variety of different shapes and sizes, and include a different quantity of lumens and cavities, and various different features and capabilities. For example, an endoscope according to various embodiments can also include other features and/or components such as, for example, irrigation and suction devices and or capabilities. In another example, optical fibers can include a variety of different quantities of fibers and the fibers can be different shapes and sizes.

In addition, an endoscope tip can include various optical components disposed in various locations and combinations not necessarily described herein. For example, lenses can be disposed adjacent (e.g., distally) of an illumination source (e.g., 38, 162, 148, 262, 348, 562) and/or an imaging device (e.g., 36, 136, 236, 382, 536). Cavities configured to receive an optical component can extend into a housing of an endoscope tip from a proximal end, a distal end, a side portion, or any other surface area of the endoscope tip. A micro-defects portion can be included in various locations within a housing and multiple micro-defects portions can be included. The micro-defects portions shown herein are merely examples of the types and patterns that can be produced, as various shapes, sizes, patterns, etc. can be provided. In some embodiments, only a single optical component is included within the endoscope tip.

An endoscope according to embodiments described herein can also be provided without the system controller and related devices described herein. For example, an endoscope can be configured to be used with other controllers, power sources, light sources, imaging devices etc., not specifically described herein. Likewise, the system controller (and related devices) described herein can be used with other configurations of an endoscope.

What is claimed is:

1. An apparatus, comprising:
   an endoscope tip including a housing, the housing being monolithically formed of a transparent material;
   at least one light source at least partially encased within the housing; and a reflector encased within the housing of the endoscope tip, at least a portion of the reflector being disposed between the light source and an exterior surface of the endoscope tip.

2. The apparatus of claim 1, wherein the light source is a light emitting diode.

3. The apparatus of claim 1, wherein the light source is a fiber optic coupled to an illumination source disposed outside the housing of the endoscope tip.

4. The apparatus of claim 1, further comprising:
a light shield encased within the housing of the endoscope tip.

5. The apparatus of claim 1, further comprising:
a light shield encased within the housing of the endoscope tip, the light shield having an opacity different than an opacity of the housing of the endoscope tip.

6. The apparatus of claim 1, wherein the housing defines a working channel configured to receive a medical tool therethrough.

7. The apparatus of claim 1, wherein the endoscope tip includes a micro defects portion defined within the housing of the endoscope tip, at least a portion of the micro-defects portion being disposed between the light source and a distal end of the endoscope tip.

8. An apparatus, comprising:
an endoscope tip including a housing, the housing being monolithically formed of a transparent material; and
at least one optical component at least partially encased within the housing,
the endoscope tip has an external surface defining an optical lens surface.

9. The apparatus of claim 1, wherein the transparent material has predefined transmissivity for a plurality of wavelengths.

10. An apparatus, comprising:
an endoscope having a distal end portion including a housing, the housing being monolithically formed with a transparent material; and
a light source at least partially encased within the housing, the housing including a micro-defects portion disposed within the transparent material of the housing.

11. The apparatus of claim 10, wherein the micro-defects portion is configured to provide a selected output shape of a beam of light produced by the light source.

12. The apparatus of claim 10, further comprising:
an optical component at least partially encased within the housing, the housing being monolithically formed about the optical component.

13. The apparatus of claim 10, wherein the housing defines a cavity, the apparatus further comprises:
an optical component at least partially disposed within the cavity of the housing, the optical component having an external surface entirely surrounded by a continuous boundary formed by the housing.

14. The apparatus of claim 10, further comprising:
an image detector at least partially encased within the housing.

15. The apparatus of claim 10, wherein the housing defines a lumen configured to receive a medical tool therethrough.

\* \* \* \* \*